US009480544B2

(12) United States Patent
Rohner et al.

(10) Patent No.: US 9,480,544 B2
(45) Date of Patent: Nov. 1, 2016

(54) DENTAL FURNACE

(71) Applicant: Ivoclar Vivadent AG, Schaan (LI)

(72) Inventors: Gottfried Rohner, Altstätten (CH);
Rudolf Jussel, Feldkirch-Gisingen (AT)

(73) Assignee: Ivoclar Vivadent AG, Schaan (LI)

( * ) Notice: Subject to any disclaimer, the term of this patent is extended or adjusted under 35 U.S.C. 154(b) by 255 days.

(21) Appl. No.: 14/135,624

(22) Filed: Dec. 20, 2013

(65) Prior Publication Data

US 2014/0113237 A1   Apr. 24, 2014

Related U.S. Application Data

(63) Continuation-in-part of application No. 14/127,609, filed as application No. PCT/EP2013/051272 on Jan. 24, 2013.

(30) Foreign Application Priority Data

Jan. 27, 2012   (EP) ...................................... 12152931
Jul. 22, 2013   (CN) ...................... 2013 2 0437085 U

(51) Int. Cl.
*F27B 17/00*   (2006.01)
*A61C 13/20*   (2006.01)
*F27B 5/18*    (2006.01)
*F27B 17/02*   (2006.01)
(Continued)

(52) U.S. Cl.
CPC ................ *A61C 13/20* (2013.01); *F27B 5/18* (2013.01); *F27B 17/025* (2013.01); *F27D 19/00* (2013.01); *F27D 21/00* (2013.01)

(58) Field of Classification Search
CPC ............................. F27B 17/025; F27D 21/02

USPC ........................ 432/1, 32; 219/390, 400, 411
See application file for complete search history.

(56) References Cited

U.S. PATENT DOCUMENTS

| 5,372,502 A | 12/1994 | Massen et al. |
| 6,287,121 B1 | 9/2001 | Guiot et al. |
| 7,108,508 B2 | 9/2006 | Hedge et al. |

(Continued)

FOREIGN PATENT DOCUMENTS

| CN | 100998522 A | 7/2007 |
| JP | H05290209 A | 11/1993 |

(Continued)

*Primary Examiner* — Gregory A Wilson
(74) *Attorney, Agent, or Firm* — Ann M. Knab; Thad McMurray

(57) ABSTRACT

The invention relates to a dental furnace comprising a firing hood equipped with a heating device that is movably supported for the opening and closing of the dental furnace relative to a base intended for receiving a dental restoration part, and further comprising a heat detection device that is directed towards an area above the base, in particular towards one or more dental restoration parts, and further comprising a control or regulating device for the dental furnace that is coupled to the heat detection device, wherein the heat detection device is configured as a thermal imaging camera (30) which is directed towards the area above the base while the firing hood (12) is partially or completely opened, and which feeds an at least two-dimensional image in the form of a matrix of the one or more inserted dental restoration parts (60) to the control or regulating device and/or to a muffle (26) that is intended for the generation of the dental restoration parts (60).

18 Claims, 4 Drawing Sheets

(51) Int. Cl.
*F27D 19/00* (2006.01)
*F27D 21/00* (2006.01)

(56) References Cited

U.S. PATENT DOCUMENTS

| | | | |
|---|---|---|---|
| 7,623,942 B2 * | 11/2009 | Touchstone | A61C 13/0004 432/226 |
| 2001/0038705 A1 | 11/2001 | Rubbert et al. | |
| 2005/0175949 A1 * | 8/2005 | Grunenfelder | A61C 13/20 432/120 |
| 2005/0244975 A1 * | 11/2005 | Rakow | G01N 33/442 436/85 |
| 2008/0237211 A1 | 10/2008 | Jussel | |
| 2009/0087818 A1 | 4/2009 | O'Brien et al. | |
| 2010/0047731 A1 * | 2/2010 | Zubler | A61C 13/20 432/45 |
| 2011/0229840 A1 | 9/2011 | Liang et al. | |
| 2013/0026157 A1 * | 1/2013 | Jussel | A61C 13/20 219/710 |
| 2013/0029280 A1 * | 1/2013 | Jussel | F27B 5/18 432/32 |
| 2013/0029281 A1 * | 1/2013 | Jussel | A61C 13/20 432/32 |
| 2015/0010876 A1 * | 1/2015 | Grunenfelder | A61C 13/20 432/45 |

FOREIGN PATENT DOCUMENTS

| | | |
|---|---|---|
| JP | 2004272357 A | 9/2004 |
| RU | 2439489 C1 | 1/2012 |

* cited by examiner

DENTAL FURNACE

CROSS-REFERENCE TO RELATED APPLICATIONS

This application is a continuation-in-part of U.S. patent application Ser. No. 14/127,609, filed Dec. 19, 2013, which is a National Stage application of International patent application PCT/EP2013/051272 filed on Jan. 24, 2013, which claims priority to European patent application No. 12152931.7 filed on Jan. 27, 2012, the disclosures of each of which are incorporated herein by reference in their entirety.

TECHNICAL FIELD

The invention relates to a dental furnace according to the preamble of claim 1 or 16, respectively, as well as to a process for controlling or regulating a dental furnace according to the preamble of claim 17.

BACKGROUND OF THE INVENTION

Firing furnaces for dental purposes have been known for a long time in which dental restoration parts are fired, sintered, debound or pressed taking into account special given firing, sintering, debinding and/or pressing parameters. In this connection it is also known that the quality of the produced dental restoration parts strongly depends on the compliance with the mentioned process parameters during the entire process.

Dental restoration parts are typically placed in the furnace individually or together on a firing chamber floor or base. For the firing process a firing hood that comprises the heating for the furnace, is combined with the firing chamber floor and is usually sealed off so that the start of the firing cycle is possible. In this connection it is advantageous if the firing hood itself is supported as to be able to be lifted and/or pivoted as vibrations of the firing chamber floor and vibrations of the dental restoration parts as a consequence thereof may then be reliably avoided.

As soon as the firing hood is closed, the actual firing, sintering, debinding or pressing process may be started wherein a hold time is typically included as a precaution.

As both in firing furnaces, sintering furnaces, debinding furnaces and pressing furnaces the materials used are sensitive to a noncompliance with the process parameters, in particular temperature and pressure, usually more sensors, in particular pressure sensors and/or temperature sensors are employed in order to detect the precise course of the process parameters and to intervene if necessary to perform a control operation.

Basically, in particular a firing, debinding and/or sintering process may be divided into several subsections, for example into a drying process or debinding process, respectively, followed by the actual firing or sintering process, respectively, which in turn is followed by a cooling process.

Drying processes are usually conducted in a furnace which still is completely open or partially open and the same applies to cooling processes.

This is especially important when processing still moist dental ceramics caused by manufacture (e.g. layering ceramics, glazes, glass solders etc.) or ceramics in which heating gradients for preventing damages for example due to cracks, bubbles, porosities, an incomplete evaporation or burning of organic materials and/or heating and cooling gradients for limiting tensions within the ceramics itself, or damages due to different temperature gradients between different framework materials (metal or ceramics) and the applied coating materials or veneers, are important.

By default today's devices work with settings that have been empirically determined. The closing or opening of the firing hood is effected in a given process, e.g. within a given time and by means of a given closing movement, e.g. linear or via fixed positions. Thereby, the firing hood can already be heated to a predefined temperature or may freely cool down.

It has already been proposed to use empirically validated models according to which for example based on the temperature measured within the furnace head the thermal energy and the heating to be expected can be estimated as a function of the distance between the hot firing hood and the dental object, and the closing movement is adjusted based on the experimentally determined models.

Moreover, it has been proposed to use thermal elements that are located in the furnace head or furnace base, namely next to the working area of the dental restoration parts to be processed, but that nevertheless cannot exactly represent the temperature of these objects. It is difficult to align these sensors according to the facts. A thermal element would have to be attached to a dental object which is not feasible in practice.

Finally it has also been proposed to direct an optical temperature instrument towards the object, for example with the aid of a beam of light (laser pointer), in order to achieve a representative measurement value of the temperature of the object. The alternatives described exhibit the disadvantage that an incorrect attachment of the sensor and/or the dental object may result in a large measurement error. Moreover, the attachment of the sensors is partially difficult, for example if the object has a powdery consistency. Moreover, the measurement position of the sensors is not obvious to the user/operator, i.e. usually the dental technician, which is especially true when several dental restorations and/or larger dental restorations are to be processed.

In view of the existing problems and also the liability risks due to incorrectly burned dental restoration parts, the burning process is normally carried out with considerable safety reserves, namely with extended hold times, during which the temperature level should adjust. The definition of extended hold times here is partially left to the user. On this occasion, however, a deterioration of the properties of the ceramics used for the firing of the dental restoration part is accepted.

SUMMARY OF THE INVENTION

In contrast to that the invention is based on the object of producing a dental furnace according to the preamble of claim 1 or 16, respectively, as well as a process according to the preamble of claim 17 that permit an improved quality of the dental restoration parts to be produced.

This object is inventively solved by the claims 1, 16 and 17, respectively. Advantageous further developments emerge from the subclaims.

According to the invention in a dental furnace a heat detection device that is embodied as a thermal imaging camera, is directed towards the area above the firing chamber floor or the base, on which the dental restoration part is positioned. The thermal imaging camera is thus directed towards the working area in which the dental restoration parts may be placed, preferably from laterally outside of the dental furnace, and is capable of detecting the thermal radiation thereof two-dimensionally.

The two-dimensional image captured by the thermal imaging camera enables the detection of a thermal matrix, namely a matrix consisting of points that each represent a temperature at a given position. With a suitable resolution, even the smallest possible dental objects may still be safely detected and the temperature thereof may be measured.

This offers a plurality of advantages:

While with a simple temperature sensor normally only a punctiform temperature detection is possible, the two-dimensional temperature detection simultaneously also enables the detection of the temperature distribution. This also enables the identification of the shape, the size, the position, the number and maybe even the type of the dental restoration parts to be processed.

According to the invention it is favorable that the temperature at one or more dental restoration parts regardless of the shape, size, mass, number and material thereof may be measured at one or more positions within the working area, i.e. the firing chamber of the furnace, at a representative position or at a position that is relevant for the process.

According to the invention it is possible to detect and identify the relevant information within the entire temperature matrix, for example the dental restoration parts, and to distinguish them from the not relevant information, e.g. background disturbances, or from structural components of the dental furnace.

Prior to the insertion of the dental restoration parts, the thermal imaging camera in case of a furnace with an open hood is directed towards the environment that typically has ambient temperature. If the dental restoration parts—that are usually placed on a firing tray which facilitates the placement and removal thereof—are placed on the furnace floor, it can be detected on the one hand that the hot furnace base has now been covered. In this way the insertion or placement of a firing tray may be detected. In turn, the removal of the firing tray would be detected, because the firing base has a temperature difference compared to the firing tray. The dental restoration parts that are not yet heated during the placement thereof and approximately have the temperature of the environment or the firing tray, respectively, on which they are placed, do not result in a change of the image in the first seconds. Only if the hot furnace hood that extends over the dental restoration parts, and the firing base on which the firing tray with the objects is placed, heats the dental restoration parts to some degree, their outline stands out from the background as a thermal matrix.

In this way, dental restoration parts that have just been inserted into the pre-heated firing chamber during the heating process and that have a low temperature (for the most part near the ambient temperature) may be identified, for example during the drying process, and thus the relevant temperature thereof or also the temperature distribution of those objects may be determined and supervised.

According to the invention it is favorable that the results and knowledge determined in this way, without any additional effort and readily can be used for the control or the regulation of the furnace. In case of a known and stationary distance between the thermal imaging camera and the firing chamber floor or working area, respectively, the size of the inserted objects may readily be estimated and calculated trigonometrically from the size of the thermal matrix.

In this way, desired process parameters that may depend on the size, can also and automatically be adjusted in the desired manner. If it is found out for example that there are large and several dental restoration parts, the heating rate, i.e. the desired increase of temperature, may be reduced at the object in order to achieve a gentle and safe drying operation.

Also in the case of several objects the process can be performed in a safe manner due to given methods. For example it is possible to control the temperature to be at maximum in order to avoid pores and cracks upon drying. In other cases for example, an averaging of the identified and relevant temperature measurement points may be advantageous. In a further design it is provided that a minimum temperature must be reached at all identified measurement points before a subsequent process follows.

In principle, it would also be possible to detect further information if the thermal imaging camera is aligned correspondingly, said further information including the type of the base employed on which the dental restoration parts are placed in the furnace, as well as the size thereof and/or the temperature thereof. This information can be inventively used in the current process step but also in a subsequent process step, for example the firing process. That way errors due to different sizes and masses of firing trays may be eliminated and the end temperature of the dental restoration parts that is to be achieved during the firing process remains independent thereof.

According to the invention the identification of the firing tray can be carried out analogously to the identification of the dental restoration parts.

At the same time the inventive thermal imaging camera allows a regulation of the preheating and/or the cooling on the basis of the temperature detected at the objects by changing the position of the furnace head relative to the furnace floor or by changing the furnace temperature in the furnace head due to the heating or the cooling or by simultaneously changing the position and the heating power.

Also the temperature itself and the temperature distribution in the area detected by the thermal imaging camera can be detected.

It is to be understood that in the same manner the position of the furnace hood relative to the dental restoration parts can be of course regulated, too. That way, the lowering of the furnace hood can be controlled and regulated in order to have the temperature decrease or temperature increase, respectively, at the previously identified dental restoration parts follow a given desired temperature course.

According to the invention it is particularly favorable that due to the course of temperature it is determined if potential liquids (e.g. residual water) necessary for the processing and production, have evaporated, and then after having interpolated a certain hold time if necessary, the lowering of the hood or the increase of temperature, respectively, can be further and automatically continued.

In the same manner it is possible according to the invention to safely reach a pregiven temperature or temperature distribution regardless of the type, number and mass of the dental restoration parts by using the thermal imaging camera with the control and regulating device. This enables a process duration tailored to the needs of the ceramic parts, namely without the safety reserves mentioned at the beginning, and also without taking any risks.

Due to the inevitably arising temperature difference between the background and the dental restoration parts, the background can quasi be masked out electronically: with the aid of a corresponding filter or image data processing routines, respectively, without further ado the detection is limited to those matrix cells whose temperature exceeds the room temperature.

While the furnace is operating, the tooth replacement, the crown or bridge or a respective multiple arrangement is placed on the firing chamber floor while the furnace hood is open and the furnace heating is switched on. Even if the furnace heating is spaced apart from the dental restoration part quite a distance, a heat transfer takes place that leads to a slow heating of the dental restoration parts. Already in this condition it can be observed via the thermal imaging camera that is directed towards the area just above the firing chamber floor that dental restoration parts are arranged there, but also the shape thereof in the two-dimensional projection can be detected.

From the course of the heating, the mass of the dental restoration parts can be concluded to a certain degree.

It is to be understood that this procedure can be applied analogously if the furnace is still warm due the previous firing cycle and the heating is still switched off. In this case typically both the firing chamber floor and the - open - hood give off heat to the dental restoration parts that because of this differ from the background having room temperature in the thermal image.

In the same manner, the thermal image detection in the case of a press furnace can be carried out by using a muffle. Typically, a muffle with a blank inserted therein is heated in a preheating furnace, typically to a temperature of 850° C. In turn, the actual press furnace can then be still warm due to the previous pressing cycle. In the open state of the furnace hood, the hot muffle is placed on the firing chamber floor in a manner known per se. The hot muffle here also results in a change of the temperature at matrix elements that previously have detected ambient temperatures or temperatures of the background, respectively. This makes it possible here as well to detect the insertion of the muffle by evaluating the temporal change of the individual thermal images.

The information gained in this manner can be used in a very simple way for the control of the furnace during the closing operation of the firing hood whereas it is to be understood that also safety monitoring or the triggering of alarms can easily be represented.

Only for the exemplary purpose the constellation is described for the case that a muffle is eccentrically placed within the firing chamber. The thermal imaging camera is able to immediately detect a lateral displacement of the matrix, and can then give an alarm or invite the user to correct the situation, respectively. Even if the displacement is not in the lateral direction but in the direction of the thermal radiation, this can be detected nevertheless. The detection is possible due to a stationary camera that is mounted opposite to the set up position of the press muffle and that at the same time can determine the geometric size of the object. If the object is placed eccentrically and too close to the camera, it appears larger in the image, and if it is further away it appears smaller.

The control or the regulation of the firing furnace or the press furnace according to the invention takes place automatically regardless of size, temperature and time wherein both the size of the dental restoration part or the muffle, respectively, and the temperature thereof are detected by the thermal imaging camera according to the invention.

In a particularly favorable embodiment according to the invention it is provided that the thermal image can be displayed —if necessary in an electronically processed manner —on a display of the furnace or on a display connected with the furnace. In this way, a visual plausibility check can be realized as well. In a further embodiment it is provided that the dental technician processes said image and if necessary even intervenes interactively, in order to change the preselected objects defined by the thermal imaging camera or to manually determine or shift the measuring point for the process management.

Typically, the thermal imaging camera is directed such that it is attached to the furnace diagonally back and detects the image thereof in particular diagonally to the front. At the opposite side of the firing chamber—as seen from above of the thermal imaging camera—typically no heat sources are present that could adversely affect the detection by the thermal imaging camera. Heat sources that are present nevertheless, such as a firing furnace that coincidentally is arranged in the viewing direction of the camera, that is opened and that is correspondingly hot, can nevertheless be distinguished from the dental restoration part. This is due to the fact that a foreign heat source has as different temporal course of temperature than the dental restoration parts inserted into the dental furnace according to the invention. The mentioned position of the camera is also favorable because through this it is more difficult for the user to inadvertently insert disturbing objects between the camera and the dental restoration parts that are to be detected.

In this connection it is of course possible to realize plausibility checks, that for example eliminate large temperatures at the beginning of the thermal treatment as being not plausible. Also, it is possible to facilitate the background differentiation via a hand movement between the background of the thermal imaging camera and the furnace as corresponding temperature gradients in subsequent images can be detected in the matrix elements not covered by the dental object.

According to the invention both the absolute temperature of the objects to be fired and the development or the change of the temperature, respectively, can be detected and evaluated at each matrix element viewed.

Moreover, a supervision beyond the actual heating process is possible. Typically, the object to be fired must not change its position during the process. This fact, too, can be used with the inventive thermal imaging camera for the error monitoring.

While in the favorable case the axis orientation of the thermal imaging camera is exactly horizontal and intersects the vertical center axis of the firing furnace or press furnace, respectively, it is also possible in a modified embodiment of the invention to tilt the axis of the thermal imaging camera, for example 15° in either direction up or down, in order to realize a still better discernability if necessary or a better detection of the dental restoration parts.

In a further modified embodiment the thermal imaging camera for a firing furnace may be pivoted along a segment of a circle of for example 90°. Due to the different positions, three-dimensional thermal images of the warming dental restoration parts can be taken and accordingly evaluated.

If necessary, the inventive thermal imaging camera can also work when the furnace hood is lowered. For this purpose, a viewing window is provided in the firing hood which viewing window is permeable to infrared radiation and allows for the longest possible visual contact with the objects to be measured even at a lowered furnace hood.

In a further embodiment the camera is attached to the firing hood, and in this case the location-based data will change with the position of the furnace hood. However, this may be taken into account correspondingly by installing a position detection device for the firing hood, and can continuously be taken into account for the control and regulation of the process.

It is especially favorable if the control device evaluates the individual matrix elements of the matrix both with respect to the temperature detected and the configuration, i.e. where there are warm regions and where there are not, and identifies them to be relevant or not relevant for a process control. For this purpose it can, for instance, identify a warm area with an upright rectangular shape as a warm muffle.

In an advantageous embodiment it is provided that the matrix elements which have been identified as being relevant are calculated to become a default value for the regulation in any desired mathematical manner, such as by forming an average value, a maximum value, an average value of maximum values of individual identified restorations, for instance also by considering the number of matrix elements and thus the size or number of objects.

In an advantageous embodiment it is provided that the control device evaluates the individual matrix elements of the matrix both with respect to the temperature detected and the configuration, i.e. where there are warm regions and where there are not, and identifies them to be relevant or not relevant for a process control.

In an advantageous embodiment it is provided that the control or regulating device detects and evaluates the thermal image of the detected object, in particular the detected dental restoration part, with respect to its relative position with regard to the base and/or the firing hood, and therefore to the dental furnace.

In an advantageous embodiment it is provided that the control or regulating device detects and evaluates the thermal image with respect to its temporal development (1. derivative) and based on the location-based change of temperature identifies the dental restorations and the matrix elements relevant for the process control, and controls the dental furnace depending on said matrix elements.

In an advantageous embodiment it is further provided that the control or regulating device controls the closing and/or opening of the firing hood depending on the temporal development of the thermal image and/or that the control or regulating device controls or regulates the temperature in the firing hood depending on the temporal development of the thermal image.

In an advantageous embodiment it is also provided that the thermal imaging camera is calibrated with respect to the temperature and that each matrix element is configured as a temperature sensor.

In an advantageous embodiment it is provided that the closing movement of the firing hood of the furnace and/or the temperature of the firing hood is regulated and/or controlled by the control device based on the temperature at matrix elements selected in the image according to a set or target course of the temperature.

In an advantageous embodiment it is provided that a display device is attached to the dental furnace or associated therewith, and that the thermal image of the detected object or objects is represented on the display device in color, wherein warm regions are represented more reddish or brighter and cold regions are represented more bluish and darker, and/or identified objects are marked in different colors and the background is displayed in greyscale, or that the identified objects are framed or highlighted in a visible manner, respectively.

In an advantageous embodiment it is provided that the thermal imaging camera is supported sideways next to the area above the base, namely outside the moving area of the firing hood, and with respect to its detection direction is directed towards objects horizontally, in particular orthogonally, with a dimensional tolerance of less than 5°.

In an advantageous embodiment it is provided that the control or regulating device comprises a filter device that hides warm regions outside the area above the base on which the object may be accommodated.

In an advantageous embodiment it is provided that an additional temperature sensor is provided for the control or regulation of the temperature of the heating device of the dental furnace, and that said temperature sensor is coupled to the control or regulating device for the adjustment to the output signal of the thermal imaging camera.

In an advantageous embodiment it is provided that the control device comprises an evaluation device, with the aid of which objects, in particular dental restoration parts, may be identified due to their thermal images and the temporal developments thereof during heating, i.e. during the closing of the firing hood, in particular with respect to their positions, shapes, dimensions and numbers.

In an advantageous embodiment it is provided that the control or regulating device comprises a storage device, in which the thermal image of a detected object and positions at which dental objects that have been identified as being relevant for the process control, may be stored.

In a further advantageous embodiment it is provided that the storage device stores the thermal image of the object during the drying or closing process and during the firing process and in particular stores the previously detected positions at which dental objects are relevant for the process control, and further uses those already detected positions for further temperature measurements beyond the drying or closing process, in particular during the cooling phase (opening process).

In an advantageous embodiment it is provided that the control device comprises an evaluation device, with the aid of which the closing of the firing furnace may be blocked if the evaluation of the thermal image reveals that the firing hood would collide with the object upon closing.

In an advantageous embodiment it is provided that the heat detection device is configured as a thermal imaging camera, is directed towards the area above the base and feeds an at least two-dimensional image of the one or more dental restoration parts accommodated therein to the control or regulating device, said image being present in the form of a matrix.

In an advantageous embodiment it is provided that the heat detection device is embodied as a thermal imaging camera and is directed towards the area above the base in case of the firing hood being open or through a suitable viewing window, and wherein a control device is provided that is fed with an at least two-dimensional image in the form of a matrix by the thermal imaging camera, said control device evaluating the detected areas of the matrix at least with respect to the temperature thereof.

In an advantageous embodiment a method according to the characterizing features of one of claims 1 to 17 is provided.

BRIEF DESCRIPTION OF THE DRAWINGS FIELD

Further advantages, details and features may be taken from the following description of two exemplary embodiments of the invention with reference to the drawings.

DETAILED DESCRIPTION

Figure 1:
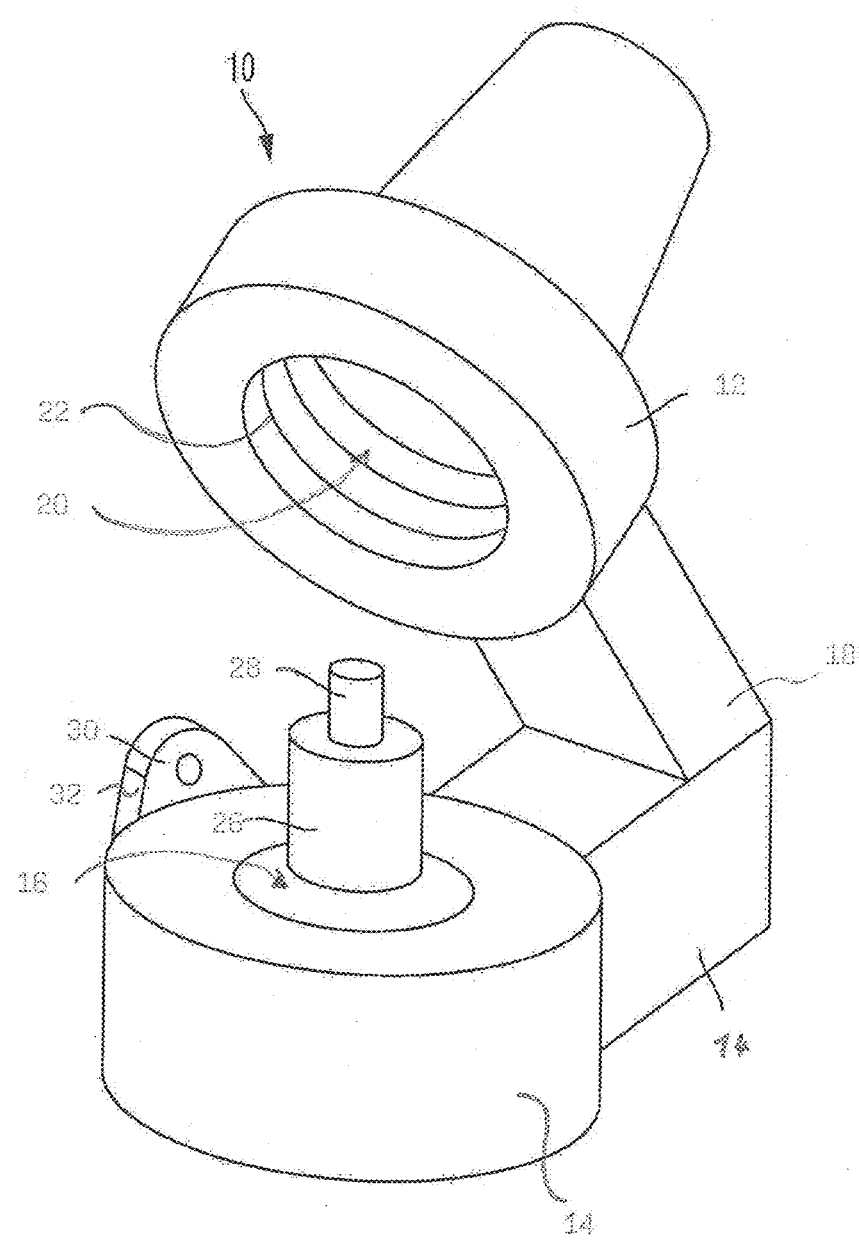
FIG. 1 shows a schematic view of an inventive dental furnace comprising a thermal imaging camera and an inserted muffle.

In FIG. 1 a dental furnace 10 is illustrated which is formed as a press furnace in the exemplary case.

The furnace comprises a firing hood 12 and a furnace bottom 14 with a firing chamber floor 16. The firing hood 12 is mounted to the furnace bottom 14 via a joint 18 which is not defined in detail and illustrated only schematically to carry out lifting and tilting movements. It is formed in the shape of a hood and therefore surrounds the firing chamber 20. At its periphery it is provided with a firing chamber heating 22 in a way known per se.

The firing chamber 20 as well as the firing hood 12 are formed in a circular manner, wherein the firing chamber has substantially the shape of a hollow cylinder. Thus, it is suitable for receiving cylindrical muffles which are used for the pressing of dental restoration parts. A muffle 26 of this type is illustrated in FIG. 1 on the firing chamber floor 16. For producing the dental restoration part the muffle is loaded with a known molding or blank 28 the diameter of which is illustrated in FIG. 1 increased in size for the sake of clarity and which is inserted into a guide channel in the muffle 26.

The blank is pressed with the help of a pressing drive (not illustrated) in the upper part of the firing hood 12.

It is to be understood that both the pressing pressure and the temperature used to carry out pressing are subject to special requirements and that the respective parameters have to be complied with accurately. Alternatively, the muffle 26 is heated from the outside by the firing chamber heating 22, such that the desired temperature in its interior, i.e. in the area of the inserted blank 28, is only reached in a delayed fashion.

Obviously, press furnaces of this type can be used to fire muffles of different diameters, such as a muffle of almost twice the diameter of the muffle 26 illustrated in FIG. 1. The height of the muffle used can also vary such that the muffle material to be heated can for instance vary by the factor of 4 from one pressing cycle to the next.

According to the invention, a thermal detection device, which is formed as a thermal imaging camera 30, is attached to the dental furnace 10, namely on the outside of the dental furnace, preferably to the furnace bottom 14.

The field of vision of the thermal imaging camera is directed to an area slightly above the firing chamber floor 16, i.e. where the muffle 26—or the dental restoration part in the case of a firing furnace—is placed. The thermal imaging camera 30 is adjusted such that it detects a slightly larger area in the horizontal and vertical direction than the size of the largest muffle 26 used. This can also be seen schematically from FIG. 2.

If necessary, the thermal imaging camera can also be provided with a lens system at its front in order to adjust the size and thus the resolution of the detection range, as required.

For protection reasons the thermal imaging camera 30 is received within a frame 32 which remains intact even if the muffle 26 is bumped inadvertently. Furthermore, it is preferably attached laterally at the rear of the furnace bottom 14, instead of laterally at the front. As a consequence, it does not get in the way on the one hand, and it is directed towards clear space on the other hand, in which typically no other heat sources are disposed.

Preferably, the orientation is selected such that the optical axis of the thermal imaging camera 30 coincides with the vertical axis of the firing chamber 20.

It is to be understood that it is also possible to select a slightly offset orientation if certain areas on the side of the muffle are to be examined specifically. It is also possible to tilt the optical axis horizontally, in the exemplary embodiment illustrated slightly to the top in an appropriate manner, in order to facilitate a better detection of the vertical center of the muffle 26.

Figure 2:
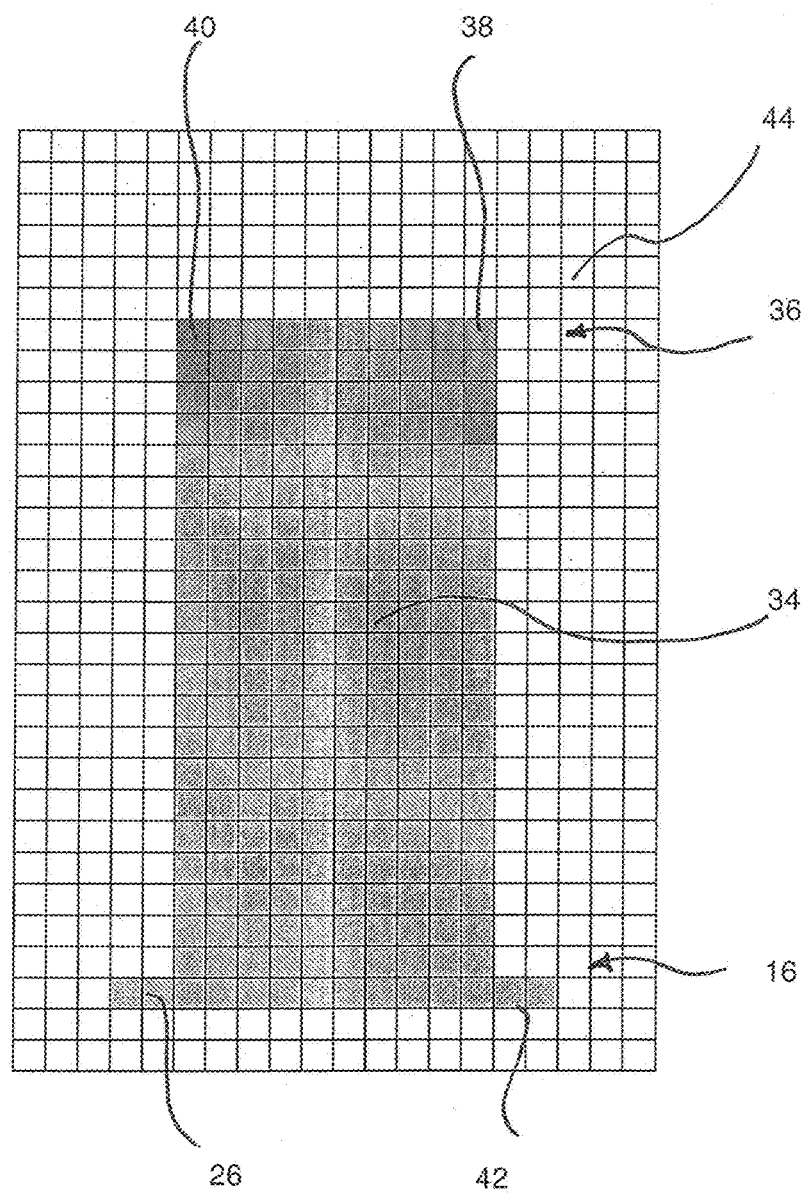
FIG. 2 shows a thermal image of the dental furnace in the embodiment according to FIG. 1.

It can be seen from FIG. 2 how a thermal image 34 is presented in the thermal imaging camera 30, if a muffle 26—which has e.g. been preheated in a preheating furnace—is supported on the firing chamber floor 16 with the firing hood 12 being opened and the firing chamber heating 22 being turned on.

In a preheating furnace the muffle is typically heated to a substantially even temperature.

In FIG. 2 only a very rough heat distribution of the thermal image 34 can be seen. It is to be understood that thermal imaging cameras typically show a color-based resolution of temperature, wherein warm areas are illustrated in yellow, hot areas in red, cooler areas in green and cold areas in blue. The color range has a substantially higher resolution than what is illustrated here such that a temperature difference of, for instance, 2° is apparent due to the corresponding color variance.

A thermal imaging camera with a resolution which is greater than what is illustrated in FIG. 2 by several orders of magnitude, for instance resolutions of 1000 pixels times 1500 pixels, can be implemented without further ado.

However, from FIG. 2 it can also be seen that the surrounding areas 44 which are illustrated without shadings in these Figures correspond to cold areas of the thermal image 34. These are illustrated in blue on the real thermal image and show the cold surrounding.

The contrast between the areas 44 and the area of the muffle 26 makes possible to detect the two-dimensional size of the muffle without further ado and to control and regulate the dental furnace 10 according to requirements.

However, according to the invention the time-dependent change of the thermal image 34 is also important which is caused by the comparison before and after the setting of the muffle.

When evaluating the thermal image 34 a plausibility test is carried out, too. Muffles, but also dental restoration parts in firing furnaces, have a predefined shape each. If hot spots appear in the area 44 of the thermal image, they cannot stem from the muffle or the dental restoration part and can thus be hidden without further ado.

With growing temperatures the contrast between the area 44 and the area 26 increases such that the muffle detection becomes sharper.

Here, the monitoring of the muffle in the heating phase, i.e. when closing the firing hood 12, is described; however, it is to be understood that it is favorable according to the invention that the thermal imaging camera 30 remains at its predefined location and that a thermal image detection is also carried out when opening the firing hood 12. Provided that the operation is failure-free, the muffle must remain at the same location as when the firing hood was closed, and here, too, the desired temperature profile can be adapted to the requirements and the lifting of the firing hood 12 and, if necessary, the turning off of the firing chamber heating 22 can be regulated and controlled.

If the resolution of the thermal imaging camera is accordingly fine, any possible cracks in the muffle can be detected which would run across the thermal image 34 as a slightly hotter line. This would equally apply to chipped gypsum pieces of the muffle, and in this case the flaw could be examined more accurately.

Even if the thermal imaging camera 30 is illustrated as being fixed to a predefined location, it is to be understood that a pivotable mounting is also possible in an alternative embodiment. The thermal imaging camera can then be pivoted from the 45° lateral rear position to the 45° lateral front position, i.e. it can be pivoted by 90° altogether. Especially in firing furnaces for dental restoration parts, this facilitates the three-dimensional detection of the dental restoration parts and insofar quasi a stereoscopic recording of a thermal image.

Thus, the inventive thermal imaging camera 30 can be used to detect flaws but also to identify the dental objects to be fired without further ado.

Figure 3:
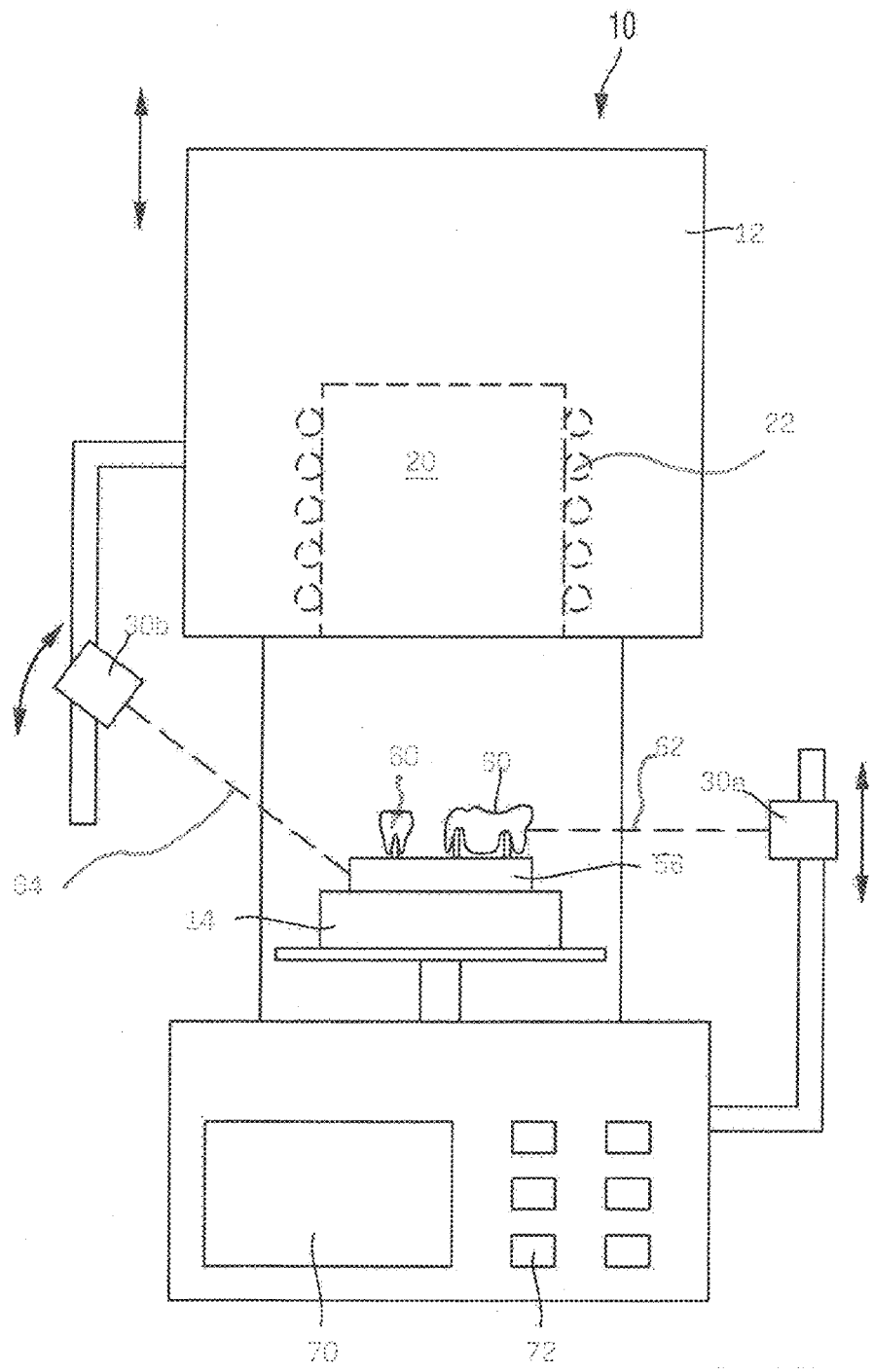
FIG. 3 shows a modified embodiment of an inventive dental furnace comprising two thermal imaging cameras.

A further embodiment of an inventive thermal imaging camera is illustrated in FIG. 3. In this solution a firing furnace 10 is used which receives dental restoration parts 60 which are placed on a firing plate 56 which is in turn supported by the furnace bottom 14. The firing chamber heating 22 is typically disposed at the outer periphery of the firing chamber 20 and partially radiates heat downwards when the firing hood 12 is open. In this way, the dental restoration parts 60 are heated even if the firing hood 12 is open. This can be detected by both thermal imaging cameras 30a and 30b which are mounted movably in the exemplary embodiment illustrated. A horizontal visual axis 62 of the thermal imaging camera 30a is directed towards the dental restoration parts 60 and detects them laterally.

In contrast, the thermal imaging camera 30b is directed towards the firing plate 56 in the exemplary embodiment illustrated, and the visual axis 64 coincides with it slightly below the dental restoration parts 60.

However, the thermal image of the thermal imaging camera 30b also detects the dental restoration parts 60, namely due to the inclined orientation of its top side. This facilitates a common and again three-dimensional detection of the thermal image or temperature image of the dental restoration parts 60.

In a way known per se, the furnace bottom 14 comprises a display device 70. Controlled by the control keys 72, it can immediately show the thermal image of the thermal imaging cameras 30a and 30b. It is additionally evaluated by an image detection device and the control of both the closing movement and the supply of the heating energy is carried out in line with the requirements.

Figure 4:
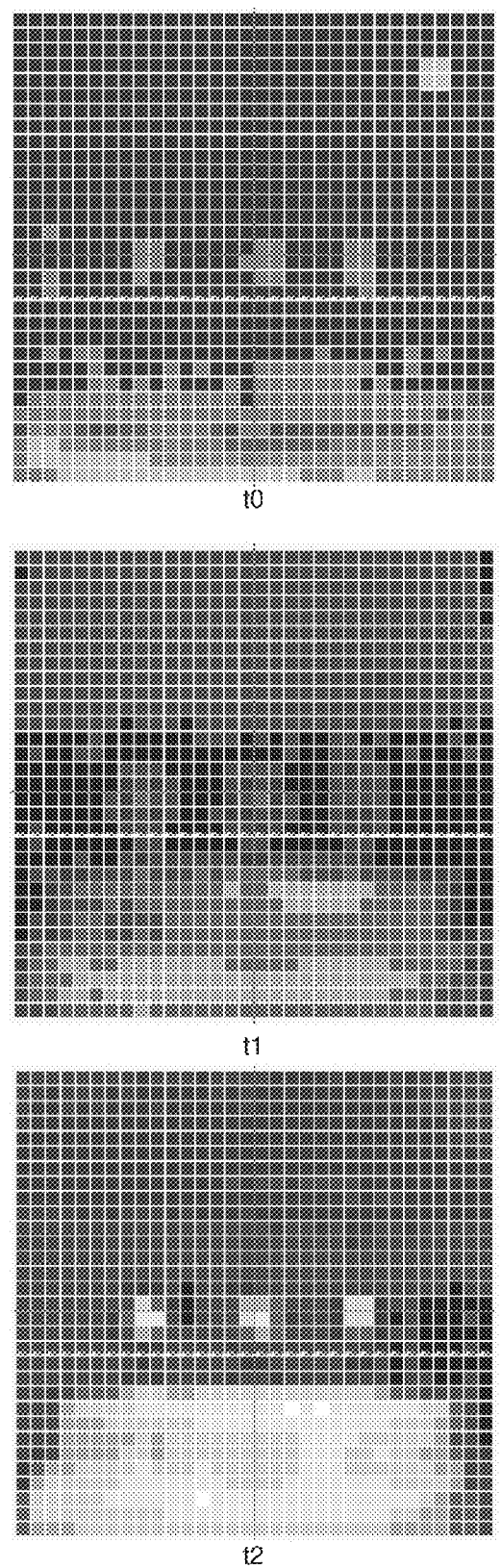
FIG. 4 shows thermal images which illustrate the heating of dental restoration parts, which have been inserted into a firing furnace, at different points in time t0, t1, t2.

FIG. 4 shows 3 thermal images which were taken at points in time t0, t1 and t2 of the working area, i.e. the areas above the base. Threshold values were used for illustrating the temperatures in the image, for the sake of a simple representation. Matrix elements which have a lower temperature than the first predefined threshold value, are illustrated almost black, and elements which have a temperature above this threshold value are illustrated brighter. At point in time t0, directly after placing the firing tray with 3 dental restorations into the firing furnace, almost no temperature differences are noticeable. The objects do not stand out against the background as their temperatures are similar. However, in the image shown a spot with a high temperature is visible in the top right corner. As this spot is not plausible the decision can be made that this is a hot object in the background and therefore these pixels do not have to be considered anymore for further analysis.

However, the inserted dental objects themselves will be heated inevitably and continuously as they have been placed below the hot furnace hood. The heating itself and the speed of the heating and whether the heating is carried out continuously can be determined and calculated by periodically storing the images in a predefined and considered time period. As can be seen, at point in time t1 the firing tray and the objects have already partially heated. At point in time t2 all objects stand out against the background clearly and sharply. Through an appropriate selection of the threshold value mentioned, a selection of objects can be carried out fast and accurately such that it might be possible in t1 already. The background interference illustrated in point in time t0 was either removed in practice or is hidden by the software and not considered in the illustration of the image anymore.

In a modified embodiment—which is not graphically illustrated here—the firing hood is stationary and the base is movable. Insofar, the firing hood is also mounted movably relative to the base. The base can e.g. be moved vertically such that the firing chamber is closed in the uppermost position of the base and in a lower position of the base the dental restoration parts can be removed. Due to the movement of the base, however, they are automatically shaken such that this embodiment is not preferred.

In a further modified embodiment instead of the firing hood a closed firing chamber is provided which can be accessed via a furnace door from the side. Here, too, a base in the form of a furnace bottom is implemented thereat which is designed for receiving one or more dental restoration parts. The thermal imaging camera can be attached to the furnace door in this solution, or to a fixed position outside the furnace door such that the interior of the furnace is detected. Thermal analysis facilitates the detection of the heating of the dental restoration parts located in the furnace.

In a further modified embodiment a viewing window permeable to infrared radiation is provided in the rear area of the furnace wall. The thermal imaging camera is directed towards this window such that the interior of the firing chamber is detected, and the surrounding space when the furnace door is open. This solution creates stronger contrasts between the hot dental restoration parts and the ambient air.

The invention claimed is:

1. A dental furnace comprising
    a firing hood equipped with a heating device that is movably supported for the opening and closing of the dental furnace relative to a base intended for receiving a dental restoration part, and
    a heat detection device that is directed towards an area above the base, towards one or more dental restoration parts, and
    a control or regulating device for the dental furnace that is coupled to the heat detection device,
    wherein the heat detection device is configured as a thermal imaging camera (30) which is directed towards the area above the base laterally from outside the furnace while the firing hood (12) is partially or completely opened, and which feeds an at least two-dimensional image in the form of a matrix of the one or more inserted dental restoration parts (60) to the control or regulating device and/or to a muffle (26) that is intended for the production of the dental restoration parts (60).

2. The dental furnace as claimed in claim 1,
    wherein the control device evaluates the individual matrix elements of the matrix both with respect to the temperature detected and the configuration by where there are warm regions (44, 26) and where there are not, and identifies the individual matrix elements as relevant or not relevant for a process control.

3. The dental furnace as claimed in claim 1, wherein the control or regulating device detects and evaluates the thermal image (34) of the detected object, with respect to its relative position with regard to the base and/or the firing hood (12) and to the dental furnace (10).

4. The dental furnace as claimed in claim 1 wherein the control or regulation device detects and evaluates the thermal image (34) with respect to its temporal development (1. derivative) and based on the location-based change of temperature identifies the dental restorations and the matrix elements relevant for the process control, and controls the dental furnace (10) depending on said matrix elements.

5. The dental furnace as claimed in claim 4, wherein the control or regulating device controls the closing and/or opening of the firing hood (12) depending on the temporal development of the thermal image (34) and/or the control or regulating device controls or regulates the temperature in the firing hood (12) depending on the temporal development of the thermal image (34).

6. The dental furnace as claimed in claim 1, wherein the thermal imaging camera (30) is calibrated with respect to the temperature and that each matrix element is configured as a temperature sensor.

7. The dental furnace as claimed in claim 1, wherein the closing movement of the firing hood (12) of the furnace and/or the temperature of the firing hood (12) is regulated and/or controlled by the control device based on the temperature at matrix elements selected in the image according to a set or target course of the temperature.

8. The dental furnace as claimed in claim 1, wherein a display device (70) is attached to the dental furnace (10) or associated therewith, and that the thermal image (34) of the detected object or objects is represented on the display device (70) in color, wherein warm regions (44, 26) are represented more reddish or brighter and cold regions (44, 26) are represented more bluish or darker, and/or identified objects are marked in different colors and the background is displayed in greyscale, or that identified objects are framed or highlighted in a visible manner.

9. The dental furnace as claimed in claim 1, wherein the thermal imaging camera (30) is supported sideways next to the area above the base, outside the moving area of the firing hood (12), and with respect to its detection direction is directed towards the objects horizontally, or orthogonally, with a dimensional tolerance of less than 5°.

10. The dental furnace as claimed in claim 1, wherein the control or regulating device comprises a filter device that hides warm regions (44, 26) outside the area above the base, on which the object may be accommodated.

11. The dental furnace as claimed in claim 1, wherein an additional temperature sensor is provided for the control or regulation of the temperature of the heating device of the dental furnace (10), and that said temperature sensor is coupled to the control or regulating device for the adjustment to the output signal of the thermal imaging camera (30).

12. The dental furnace as claimed in claim 1, wherein the control device comprises an evaluation device, with the aid of which objects, may be identified due to their thermal image (34) and the temporal development thereof during the heating, or during the closing of the firing hood (12), with respect to the positions, shapes, dimensions and numbers.

13. The dental furnace as claimed in claim 1, wherein the control or regulating device comprises a storage device, in which the thermal image (34) of a detected object and positions at which dental objects that have been identified as being relevant for the process control may be stored.

14. The dental furnace as claimed in claim 13, wherein the storage device stores the thermal image (34) of the object during the drying or closing process and during the firing process and stores the previously detected positions at which dental objects are relevant for the process control, and further uses those already detected positions for further temperature measurements beyond the drying or closing process, during the cooling phase (opening process).

15. The dental furnace as claimed in claim 1, wherein the control device comprises an evaluation device, with the aid of which the closing of the firing furnace may be blocked if the evaluation of the thermal image (34) reveals that the firing hood (12) would collide with the object upon closing.

16. A dental furnace comprising
a heating device for the heating of a firing chamber that extends above a base intended for accommodating a dental restoration part (60), and
a heat detection device that is directed towards an area above the base, towards one or more dental restoration parts (60),
a furnace door and
a control or regulating device for the dental furnace (10) to which the heat detection device is coupled,
wherein the heat detection device is configured as a thermal imaging camera (30), is directed towards the area above the base and feeds an at least two-dimensional image of the one or more dental restoration parts (60) accommodated therein to the control or regulating device, said image being present in the form of a matrix.

17. A process for controlling a dental furnace that heats a dental restoration part via a closable firing hood, wherein a heat detection device is directed towards an area above a base that is coupled to the dental furnace, wherein the heat detection device is embodied as a thermal imaging camera (30) and is directed towards the area above the base in case of the firing hood (12) being open or through a suitable viewing window, and wherein a control device is provided that is fed with an at least two-dimensional image in the form of a matrix by the thermal imaging camera (30), said control device evaluating the detected areas (44, 26) of the matrix at least with respect to the temperature thereof.

18. The process as claimed in claim 17, carried out at a dental furnace that is characterized by comprising
a firing hood equipped with a heating device that is movably supported for the opening and closing of the dental furnace relative to a base intended for receiving a dental restoration part, and
a heat detection device that is directed towards an area above the base, towards one or more dental restoration parts, and a control or regulating device for the dental furnace that is coupled to the heat detection device, wherein the heat detection device is configured as a thermal imaging camera (30) which is directed towards the area above the base laterally from outside the furnace while the firing hood (12) is partially or completely opened, and which feeds an at least two-dimensional image in the form of a matrix of the one or more inserted dental restoration parts (60) to the control or regulating device and/or to a muffle (26) that is intended for the production of the dental restoration parts (60).

* * * * *